(12) United States Patent
Norman et al.

(10) Patent No.: US 9,216,303 B2
(45) Date of Patent: Dec. 22, 2015

(54) MASCARA FORMULATION

(71) Applicant: Mary Kay Inc., Dallas, TX (US)

(72) Inventors: Greg Norman, Bedford, TX (US); Maria Milagros Sanchez, Dallas, TX (US)

(73) Assignee: MARY KAY INC., Addison, TX (US)

( * ) Notice: Subject to any disclaimer, the term of this patent is extended or adjusted under 35 U.S.C. 154(b) by 171 days.

(21) Appl. No.: 13/724,194

(22) Filed: Dec. 21, 2012

(65) Prior Publication Data

US 2013/0164241 A1    Jun. 27, 2013

Related U.S. Application Data

(60) Provisional application No. 61/579,980, filed on Dec. 23, 2011.

(51) Int. Cl.
| | | |
|---|---|---|
| *A61K 8/84* | (2006.01) | |
| *A61Q 1/10* | (2006.01) | |
| *A61K 8/81* | (2006.01) | |

(52) U.S. Cl.
CPC ............ *A61Q 1/10* (2013.01); *A61K 8/8182* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 5,621,012 A | 4/1997 | Schonrock et al. | 514/629 |
| 5,776,443 A | 7/1998 | Vinski et al. | 424/70.12 |
| 6,036,968 A | 3/2000 | Roulier et al. | 424/401 |
| 6,306,377 B1 | 10/2001 | Coppola et al. | 424/70.1 |
| 6,306,407 B1 | 10/2001 | Castro et al. | 424/401 |
| 6,524,565 B1 | 2/2003 | Loginova et al. | 424/70.7 |
| 6,596,286 B2 | 7/2003 | Castro et al. | 424/401 |
| 6,774,175 B2 | 8/2004 | Ascione et al. | 524/523 |
| 7,223,383 B2 | 5/2007 | McNamara | 424/59 |
| 7,241,452 B2 | 7/2007 | Veeger et al. | 424/401 |
| 7,323,162 B2 | 1/2008 | Martin et al. | 424/64 |
| 7,416,783 B2 | 8/2008 | Higashi et al. | 428/403 |
| 7,431,919 B2 | 10/2008 | Travkina et al. | 424/70.7 |
| 7,919,105 B2 | 4/2011 | Blin et al. | 424/401 |
| 2002/0086039 A1* | 7/2002 | Lee et al. | 424/401 |
| 2007/0020209 A1* | 1/2007 | Zamyatin et al. | 424/63 |
| 2007/0025943 A1 | 2/2007 | Patel | 424/70.7 |
| 2009/0010855 A1* | 1/2009 | Lepilleur et al. | 424/47 |
| 2009/0068255 A1* | 3/2009 | Yu et al. | 424/450 |
| 2010/0092417 A1* | 4/2010 | Narebski et al. | 424/70.7 |
| 2010/0204341 A1 | 8/2010 | Yu et al. | 514/770 |

FOREIGN PATENT DOCUMENTS

| | | | |
|---|---|---|---|
| WO | WO2009036030 | * | 3/2009 |
| WO | WO 2011/063482 | | 6/2011 |

OTHER PUBLICATIONS

International Cosmetic Ingredient Dictionary and Handbook, 12th Edition 2008, vol. 1, pp. 49.
International Cosmetic Ingredient Dictionary and Handbook, 12th Edition 2008, vol. 2, pp. 1674.
International Cosmetic Ingredient Dictionary and Handbook, 12th Edition 2008, vol. 2, pp. 1773-1774.

* cited by examiner

*Primary Examiner* — Peter J Reddig
*Assistant Examiner* — Sarah Chickos
(74) *Attorney, Agent, or Firm* — Norton Rose Fulbright US LLP

(57) ABSTRACT

Mascara primer and mascara formulations are disclosed.

11 Claims, No Drawings

MASCARA FORMULATION

CROSS REFERENCE TO RELATED APPLICATIONS

This application claims the benefit of U.S. Provisional Application No. 61/579,980, filed Dec. 23, 2011. The contents of the referenced application are incorporated into the present application by reference.

BACKGROUND OF THE INVENTION

A. Field of the Invention

The present invention relates generally to mascara formulations ranging from primer formulations, water proof formulations, and lengthening formulations.

B. Description of Related Art

Current mascaras on the market tend to lack the ability to sufficiently remain on eye lashes if subjected to external forces such as rubbing or water. Attempts to solve such problems have produced mascaras that do not provide the desired thickening or lengthening effect or become so difficult to remove that the eye lashes are damaged after such formulations are removed.

SUMMARY OF THE INVENTION

The inventor has discovered a set of mascara formulations that provide the lengthening and thickening effect for eye lashes, are easy to remove, and do not result in damage to eye lashes upon removal.

In one instance, there is disclosed a primer formulation that can be directly applied to the eye lashes, and can dry relatively quickly. This allows the user to apply a second mascara formulation onto the already applied primer formulation, which creates the desired staying power or substantivity for the second mascara formulation. Further, the primer formulation is easily washed from the lashes, which result in ease of removability of the second mascara formulation. Thus, the primary formulation can be used to prime the eye lashes so that a second mascara formulation can be applied. The primer formulation can include an aqueous base and 1 to 3% by weight of a polymer film former, wherein the aqueous base comprises 85 to 95% by weight of water, and wherein the polymer film former is polyquaternium-69, wherein the composition is capable of drying within 30 seconds or within 60 seconds after application to eye lashes. The terms "dry," "dries," "drying" or any variation thereof means that the primer composition is in a un-flowable state. By way of example, a composition of the present invention that dries within 30 or 60 seconds after application to eye lashes is in an un-flowable state. The primer composition can further include alcohol, triethanolamine, acrylic acid/VP crosspolymer, PEG-12 dimethicone, glycerin, benzyl alcohol, panthenol, chlorphenesin, hydroxypropyl cyclodextrin, disodium EDTA, phytantriol or hydrolyzed wheat protein, and iodopropynyl butylcarbamate. In certain aspects, the mascara primer composition includes 2 to 4% by weight of alcohol, 0.5 to 2% by weight of triethanolamine, 0.5 to 2% by weight of acrylic acid/VP crosspolymer, 0.5 to 2% by weight of PEG-12 dimethicone, 0.5 to 2% by weight of glycerin, 0.1 to 1% by weight of benzyl alcohol, 0.1 to 1% by weight of panthenol, 0.1 to 1% by weight of chlorphenesin, 0.01 to 0.1% by weight of hydroxypropyl cyclodextrin, 0.01 to 0.1% by weight of disodium EDTA, 0.01 to 0.1% by weight of phytantriol or hydrolyzed wheat protein, and 0.001 to 0.1% by weight of iodopropynyl butylcarbamate. The composition can be transparent, colorless and/or clear. The composition can be an aqueous solution. In certain instances, the composition is not an emulsion. Also disclosed is a method of applying any one of the mascara primer compositions to eye lashes comprising applying any one of said compositions to eye lashes with an applicator, wherein any one of said compositions dries within 30 seconds or within 60 seconds after application to said eye lashes. An applicator can include a wand portion that is dipped or placed into the primer composition and then subsequently applied to the eye lashes.

Also disclosed is a mascara formulation that has the ability to lengthen or increase the length of a person's eye lashes. This lengthening process is achieved by using a combination of synthetic fibers which build along the hair shaft in combination with polymeric and natural film formers, which act to hold the fibers in place and also act to lengthening the lashes. This formulation is less viscous when compared with mascara formulations on the market, which also enhances the ease of application and increases even coverage of the formulation to the hair shaft. The inventors discovered that a combination of particular ingredients brings about an excellent lengthening effect of eye lashes. In this regard, the mascara composition includes: (a) a combination of synthetic fibers, polymeric film formers, and a natural film former in an amount effective to lengthening eye lashes; and (b) a base, wherein the synthetic fibers are nylon 6, the polymeric film formers are PPG-17/IPDI/DMPA Copolymer and Acrylates/Ethylhexyl Acrylate Copolmer, and the natural film former is acacia senegal gum extract. The ratio of synthetic fibers to polymeric film formers can range from 0.10 to 0.30 or from 0.15 to 0.20. The ratio of synthetic fibers to the natural film former can range from 0.20 to 0.30 or from 0.22 to 0.26. The ratio of polymeric film formers to the natural film former can range from 1.0 to 2.0 or from 1.0 to 1.5. The composition can be formulated as an oil-in-water emulsion. The oil phase can include the polymeric film formers and natural film former. The oil phase can further include a wax and/or an emulsifier. The wax can be beeswax, carnauba wax, or candelilla wax or a combination of two or all of said waxes. The amount of said wax(es) present within the composition can be 5 to 10%. The oil phase can be 15 to 25% by weight of the composition. The emulsion can also include a second dispersed phase (with the first dispersed phase being the aforementioned oil phase), wherein the second dispersed phase comprises volatile solvents. The second dispersed phase can be 3 to 5% by weight of the composition. The volatile solvents can be cyclopentasiloxane or dimethicone or a combination of both. In particular aspects, the base can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, and/or all 38 of water, iron oxides, beeswax, glyceryl stearate, paraffin, cyclopentasiloxane, stearic acid, carnauba wax, butylene glycol, VP/Eicosene copolymer, triethanolamine, methyl methacrylate crosspolymer, silica, polyvinylpyrrolidone, propylene glycol, candelilla wax, trimethylsiloxysilicate, polyglyceryl-6 polyricinoleate, polytetrafluoroethylene, dimethicone, palmitic acid, hydroxyethylcellulose, diazolidinyl urea, panthenol, methylparaben, tocopheryl acetate, simethicone, sodium polymethacrylate, phytantriol or hydrolyzed wheat protein, disodium EDTA, sodium acrylate/sodium acryloyldimethyl taurate copolymer, propylparaben, phenoxyethanol, cyclohexasiloxane, aminomethyl propanol, cyclotetrasiloxane, ethylparaben, and/or titanium dioxide. In even more particular aspects, the base can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, and/or all 38 of 45 to 55% by weight of water, 5 to 10% by weight of iron oxides, 3 to 5% by weight of beeswax, 3 to 5% by weight of glyceryl stearate, 2 to 4% by weight of paraffin, 2 to 4% by weight of cyclopentasiloxane, 2 to 4% by weight of stearic acid, 2 to 4% by weight of carnauba wax, 1 to 3% by weight of butylene glycol, 1 to 3% by weight of VP/Eicosene copolymer, 1 to 3% by weight of triethanolamine, 1 to 3% by weight of methyl methacrylate crosspolymer, 0.5 to 2% by weight of silica, 0.5 to 2% by weight of polyvinylpyrrolidone, 0.1 to 1% by weight of propylene glycol, 0.1 to 1% by weight of candelilla wax, 0.1 to 1% by weight of trimethylsiloxysilicate, 0.1 to 1% by weight of polyglyceryl-6 polyricinoleate, 0.1 to 1% by weight of polytetrafluoroethylene, 0.1 to 1% by weight of dimethicone, 0.1 to 1% by weight of palmitic acid, 0.1 to 1% by weight of hydroxyethylcellulose, 0.1 to 1% by weight of diazolidinyl urea, 0.1 to 1% by weight of panthenol, 0.01 to 0.2% by weight of methylparaben, 0.01 to 0.2% by weight of tocopheryl acetate, 0.01 to 0.1% by weight of simethicone, 0.01 to 0.1% by weight of sodium polymethacrylate, 0.01 to 0.1% by weight of phytantriol or hydrolyzed wheat protein, 0.01 to 0.1% by weight of disodium EDTA, 0.01 to 0.1% by weight of sodium acrylate/sodium acryloyldimethyl taurate copolymer, 0.01 to 0.1% by weight of propylparaben, 0.01 to 0.1% by weight of phenoxyethanol, 0.01 to 0.1% by weight of cyclohexasiloxane, 0.01 to 0.1% by weight of aminomethyl propanol, 0.001 to 0.1% by weight of cyclotetrasiloxane, 0.001 to 0.1% by weight of ethylparaben, and/or 0.0001 to 0.1% by weight of titanium dioxide. Also disclosed is a method of applying any one of the mascara compositions to eye lashes comprising applying any one of said compositions to eye lashes with an applicator, wherein any one of said compositions increases the length of the hair shaft when compared with a hair shaft that does not have any one of said compositions applied thereto. An applicator can include a wand portion that is dipped or placed into the primer composition and then subsequently applied to the eye lashes.

In yet another embodiment there is disclosed a mascara formulation that can achieve a full volume and defined look when applied to a person's eye lashes. It was discovered that a combination of aqueous thickeners can be used to thicken the mascara while also increasing the elasticity and film forming properties of the mascara to enhance the volume and also increase the length of the hair shaft. A combination of natural and synthetic waxes are used to provide structure to the mascara and also increase the volume of the hair shaft. A combination of silicone fluids and a powder is used to enhance the ease of application/spreadability of the mascara onto eye lashes while also conditioning the hair shaft. These discovered combinations result in a well-performing mascara product. In one aspect, there is disclosed a mascara composition that is capable of increasing the length or volume of a person's eye lashes, the composition comprising: (a) a combination of aqueous thickeners comprising hydroxyethylcellulose, acacia gum, and polyvinylpyrrolidone in an amount effective to increase the length or volume of the eye lashes; (b) a combination of natural and synthetic waxes comprising beeswax, carnauba wax, and paraffin in an amount effective to increase the volume of the eye lashes; (c) a combination of silicone fluids and a powder in an amount effective to increase the spreadability of the composition on the eye lashes, wherein the silicone fluids comprise methyl trimethicone, dimethicone, dimethiconol, cyclohexasiloxane, and cyclopentasiloxane, and wherein the powder comprises ultramarine or silica or both; and (d) a base. The composition can include (a) 3 to 5% by weight of the combination of aqueous thickeners; (b) 10 to 13% by weight of the combination of natural and synthetic waxes; and (c) 5 to 10% by weight of the combination of silicone fluids and the powder. The composition can be formulated as an oil-in-water emulsion. The oil phase comprises said combination of natural and synthetic waxes. The oil phase can further include a film former and an emulsifier. The oil phase can include 20 to 25% by weight of the composition. The composition can further include a second dispersed phase that is different from the oil phase, wherein the second dispersed phase comprises volatile solvents. The second dispersed phase can include 5 to 10% by weight of the composition. The volatile solvents can include alcohol, methyl trimethicone, and/or dimethicone. In particular aspects, the base can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and/or all 31 of water, acrylates/ethylhexyl acrylate copolymer, alcohol, chromium oxide and or iron oxide, glyceryl stearate, stearic acid, methyl methacrylate crosspolymer, butylene glycol, VP/Eicosene copolymer, triethanolamine, silica, propylene glycol, mica, diazolidinyl urea, titanium dioxide, panthenol, a dye or colorant, methyl paraben, tocopheryl acetate, isostearic acid, sodium polymethacrylate, ethylene/methacrylate copolymer, disodium EDTA, phytantriol or hydrolyzed wheat protein, hydrogenated polyisobutene, laureth-21, propylparaben, isopropyl titanium triisostearate, phenoxyethanol, palmitic acid, and/or benzoic acid. In even more particular aspects, the base can include any one of, any combination of, all of, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and/or all 31 of 40 to 50% by weight of water, 3 to 7% by weight of acrylates/ethylhexyl acrylate copolymer, 3 to 7% by weight of alcohol, 3 to 7% by weight of chromium oxide and or iron oxide, 3 to 5% by weight of glyceryl stearate, 2 to 5% by weight of stearic acid, 1 to 3% by weight of methyl methacrylate crosspolymer, 1 to 3% by weight of butylene glycol, 1 to 3% by weight of VP/Eicosene copolymer, 1 to 3% by weight of triethanolamine, 1 to 3% by weight of silica, 0.1 to 1% by weight of propylene glycol, 0.1 to 1% by weight of mica, 0.1 to 1% by weight of diazolidinyl urea, 0.1 to 1% by weight of titanium dioxide, 0.1 to 1% by weight of panthenol, 0.1 to 1% by weight of a dye or colorant, 0.1 to 1% by weight of methyl paraben, 0.001 to 0.2% by weight of tocopheryl acetate, 0.001 to 0.2% by weight of isostearic acid, 0.001 to 0.2% by weight of sodium polymethacrylate, 0.001 to 0.2% by weight of ethylene/methacrylate copolymer, 0.001 to 0.2% by weight of disodium EDTA, phytantriol or hydrolyzed wheat protein, 0.001 to 0.2% by weight of hydrogenated polyisobutene, 0.001 to 0.2% by weight of laureth-21, 0.001 to 0.2% by weight of propylparaben, 0.001 to 0.2% by weight of isopropyl titanium triisostearate, 0.001 to 0.2% by weight of phenoxyethanol, 0.001 to 0.2% by weight of palmitic acid, and/or 0.001 to 0.2% by weight of benzoic acid. Also disclosed is a method of applying any one of the mascara compositions to eye lashes comprising applying any one of said compositions to eye lashes with an applicator, wherein any one of said compositions increases the length or volume of the hair shaft when compared with a hair shaft that does not have any one of said compositions applied thereto. An applicator can include a wand portion that is dipped or placed into the primer composition and then subsequently applied to the eye lashes.

In yet another embodiment there is disclosed a water-resistant mascara formulation that can be used to increase the volume and length of a hair shaft such as an eye lash. Water-resistance means that the composition has the ability to remain on the hair shaft despite being subjected to water such as rinsing of a face, rain, or tears. It was discovered that a combination of a gel, a silicone resin solution, a hydrogenated rosin, and powder can be used to create such a mascara. In one instance, there is disclosed a water-resistant mascara composition that is capable of increasing the length or volume of a person's eye lashes, the composition comprising: (a) a gel comprising isododecane, quaternium-90 bentonite, and propylene carbonate; (b) a silicone resin solution comprising polypropylsilsesquioxane and isododecane; (c) glyceryl hydrogenated rosinate; and (d) a powder comprising silica, ethylene/methacrylate copolymer, and isopropyl titanium triisostearate, wherein the composition includes less than 10% by weight of water and is water-resistant. The composition can include: (a) 35 to 45% by weight of the gel; (b) 5 to 10% by weight of the silicone resin solution; (c) 2 to 5% by weight of the glyceryl hydrogenated rosinate; and (d) 1 to 3% by weight of the powder. In certain aspects, the composition includes less than 9, 8, 7, or 6% by weight of the composition of water or includes 4 to 6% by weight of water. The composition can also include a fiber (e.g., nylon-6). In some instances, the composition can further include any one of, any combination of, all of, or at least 1, 2, 3, 4, 5, 6, 7, 8, 9, 10, 11, 12, 13, 14, 15, and/or all 16 of iron oxide, beeswax, carnauba wax, polyethylene, methyl methacrylate crosspolymer, propylene carbonate, VP/eicosene copolymer, phenoxyethanol, cellulose, hydrogenated polycyclopentadiene, capryl glycol, nylon-6, tocopherol acetate, panthenol, butylated hydroxyanisole, and/or phytantriol or hydrolyzed wheat protein. In particular instances, the composition can further include any one of, any combination of, all of, or at least 1, 2, 3, 4, 5, 6, 7, 8, 9, 10, 11, 12, 13, 14, 15, and/or all 16 of 3 to 7% by weight of iron oxide, 3 to 7% by weight of beeswax, 3 to 7% by weight of carnauba wax, 3 to 7% by weight of polyethylene, 1 to 3% by weight of methyl methacrylate crosspolymer, 0.5 to 2% by weight of propylene carbonate, 0.5 to 2% by weight of VP/eicosene copolymer, 0.5 to 2% by weight of phenoxyethanol, 0.5 to 2% by weight of cellulose, 0.5 to 2% by weight of hydrogenated polycyclopentadiene, 0.5 to 2% by weight of capryl glycol, 0.01 to 0.2% by weight of nylon-6, 0.01 to 0.2% by weight of tocopherol acetate, 0.01 to 0.2% by weight of panthenol, 0.01 to 0.2% by weight of butylated hydroxyanisole, and/or 0.01 to 0.2% by weight of phytantriol or hydrolyzed wheat protein. In another embodiment, the composition can further include any one of, any combination of, all of, or at least 1, 2, 3, 4, 5, 6, 7, 8, 9, 10, 11, 12, 13, 14, 15, and/or all 16 of iron oxide, beeswax, carnauba wax, polyethylene, methyl methacrylate crosspolymer, nylon-6, VP/eicosene copolymer, propylene carbonate, silica, phenoxyethanol, hydrogenated polycycloepntadiene, caprylyl glycol, tocopherol acetate, panthenol, phytantriol or hydrolyzed wheat protein, and/or titanium dioxide. In yet another embodiment, the composition can further include any one of, any combination of, all of, or at least 1, 2, 3, 4, 5, 6, 7, 8, 9, 10, 11, 12, 13, 14, 15, and/or all 16 of 3 to 7% by weight of iron oxide, 3 to 7% by weight of beeswax, 3 to 7% by weight of carnauba wax, 3 to 7% by weight of polyethylene, 1 to 3% by weight of methyl methacrylate crosspolymer, 1 to 3% by weight of nylon-6, 0.5 to 2% by weight of VP/eicosene copolymer, 0.5 to 2% by weight of propylene carbonate, 0.5 to 2% by weight of silica, 0.5 to 2% by weight of phenoxyethanol, 0.5 to 2% by weight of hydrogenated polycycloepntadiene, 0.5 to 2% by weight of caprylyl glycol, 0.01 to 0.5% by weight of tocopherol acetate, 0.01 to 0.5% by weight of panthenol, 0.01 to 0.5% by weight of phytantriol or hydrolyzed wheat protein, and/or 0.0001 to 0.1% by weight of titanium dioxide. Also disclosed is a method of applying any one of the mascara compositions to eye lashes comprising applying any one of said compositions to eye lashes with an applicator, wherein any one of said compositions increases the length or volume of the hair shaft when compared with a hair shaft that does not have any one of said compositions applied thereto. An applicator can include a wand portion that is dipped or placed into the primer composition and then subsequently applied to the eye lashes. The composition, after being applied to eye lashes, can be subjected to water such as rinsing or tears without being removed from the eye lashes.

Each of the aforementioned mascaras can increase the length and volume of a hair shaft. For instance, the formulations can increase the volume of a hair shaft by 2 times, 3 times, 4 times, or 5 times the original volume of the hair shaft, with volume being measured by standard mathematical equations for the shape of the shaft (e.g., cylinder, irregular prism, rectangle, etc., as the shape of a given shaft may vary, so may the appropriate equation). The length of the hair shaft can also be lengthened, which can be measured by determining the length of a hair shaft prior to and post application of a given mascara.

It is also contemplated that the viscosity of any of the compositions can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. Examples of UVA and UVB ingredients that can be used include titanium dioxide, mica, zinc oxide, avobenzone, octocrylene, oxybenzone, octinoxate, benzophenone, homosalate, or octisalate, or any combination thereof. Other examples include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Also contemplated are kits that include any one of the compositions disclosed throughout the specification and claims. In certain embodiments, the composition is comprised in a container. The container can be a bottle, dispenser, or package. In more particular embodiments, the container can include a base and a cap, with the cap further including an applicator such as a wand with a brush, comb, or wire structure at the distal end of the wand. The container can include indicia on its surface. The indicia can be a word, an abbreviation, a picture, or a symbol.

The compositions and methods for their use can "comprise," "consist essentially of," or "consist of" any of the ingredients disclosed throughout the specification. Consisting essentially of means that inclusion of additional ingredients in the compositions do not materially affect the beneficial properties of the compositions such as priming eye lashes for subsequent application of a mascara, increasing the volume of the eye lashes, and/or increasing the length of the eye lashes.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

A "non-volatile oil" includes those substance that will not evaporate at ordinary or room temperature.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," "treating," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

The inventor discovered a set of mascaras and a primer that can be used to lengthening eye lashes, increase the volume of eye lashes, increase the wearability of mascaras (primer), and increase the water-resistance of the mascaras. Each of these mascaras and the primer rely on certain combinations of ingredients that bring about their desired effects. These combinations are described in the following examples.

Examples

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

The Table 1 composition describes a mascara primer that can be applied to eye lashes. The mascara was clear and when applied it was not visible to the eye. The formulation dries within 60 seconds after application to the eye lashes.

TABLE 1*

| Ingredient | % Concentration (by weight) |
| --- | --- |
| Water | 90 |
| Polyquaternium-69 | 2 |
| Alcohol Denatured | 2.74 |
| Excipients** | q.s. |

*Prepare by mixing the ingredients under heat until uniform and then cool to room temperature (20-25° C.).
**The formulation can be filled out with additional ingredients to have a desired consistency, viscosity, and tactile property. Excipients used for this formula included the following in the following approximate amounts: 2 to 4% by weight of alcohol; 0.5 to 2% by weight of triethanolamine; 0.5 to 2% by weight of acrylic acid/VP crosspolymer; 0.5 to 2% by weight of PEG-12 dimethicone; 0.5 to 2% by weight of glycerin; 0.1 to 1% by weight of benzyl alcohol; 0.1 to 1% by weight of panthenol; 0.1 to 1% by weight of chlorphenesin; 0.01 to 0.1% by weight of hydroxypropyl cyclodextrin; 0.01 to 0.1% by weight of disodium EDTA; 0.01 to 0.1% by weight of phytantriol or hydrolyzed wheat protein; and 0.001 to 0.1% by weight of iodopropynyl butylcarbamate.

The Table 2 composition describes a mascara that was shown to increase the length of a hair shaft while still being easy to apply and remove from the hair shaft.

TABLE 2*

| Ingredient | % Concentration (by weight) |
| --- | --- |
| Water | 50 |
| Nylon 6 | 0.7 |
| PPG/IPDI/DMPA Copolymer | 3 |
| Acrylates/Ethylhexyl Acrylate Copolymer | 1 |
| Acacia Senegal Gum Extract | 3 |
| Excipients** | q.s. |

*Prepare by mixing the ingredients under heat until uniform and then cool to room temperature (20-25° C.).
**The formulation can be filled out with additional ingredients to have a desired consistency, viscosity, and tactile property. Excipients used for this formula included the following in the following approximate amounts: 3 to 5% by weight of beeswax; 3 to 5% by weight of glyceryl stearate; 2 to 4% by weight of paraffin; 2 to 4% by weight of cyclopentasiloxane; 2 to 4% by weight of stearic acid; 2 to 4% by weight of carnauba wax; 1 to 3% by weight of butylene glycol; 1 to 3% by weight of VP/Eicosene copolymer; 1 to 3% by weight of triethanolamine; 1 to 3% by weight of methyl methacrylate crosspolymer; 0.5 to 2% by weight of silica; 0.5 to 2% by weight of polyvinylpyrrolidone; 0.1 to 1% by weight of propylene glycol; 0.1 to 1% by weight of candelilla wax; 0.1 to 1% by weight of trimethylsiloxysilicate; 0.1 to 1% by weight of polyglyceryl-6 polyricinoleate; 0.1 to 1% by weight of polytetrafluoroethylene; 0.1 to 1% by weight of dimethicone; 0.1 to 1% by weight of palmitic acid; 0.1 to 1% by weight of hydroxyethylcellulose; 0.1 to 1% by weight of diazolidinyl urea; 0.1 to 1% by weight of panthenol; 0.01 to 0.2% by weight of methylparaben; 0.01 to 0.2% by weight of tocopheryl acetate; 0.01 to 0.1% by weight of simethicone; 0.01 to 0.1% by weight of sodium polymethacrylate; 0.01 to 0.1% by weight of phytantriol or hydrolyzed wheat protein; 0.01 to 0.1% by weight of disodium EDTA; 0.01 to 0.1% by weight of sodium acrylate/sodium acryloyldimethyl taurate copolymer; 0.01 to 0.1% by weight of propylparaben; 0.01 to 0.1% by weight of phenoxyethanol; 0.01 to 0.1% by weight of cyclohexasiloxane; 0.01 to 0.1% by weight of aminomethyl propanol; 0.001 to 0.1% by weight of cyclotetrasiloxane; 0.001 to 0.1% by weight of ethylparaben; and 0.0001 to 0.1% by weight of titanium dioxide.

The Table 3 composition describes a mascara that was shown to increase the length of the eyelashes and also increase the volume of a hair shaft while still being easy to apply and remove from the shaft.

TABLE 3*

| Ingredient | % Concentration (by weight) |
| --- | --- |
| Water | 44 |
| Hydroxyethylcellulose | 0.4 |
| Acacia Senegal Gum Extract | 3 |
| Polyvinylpyrrolidone | 1 |
| Beeswax | 5 |
| Carnauba Wax | 4 |
| Paraffin | 4 |
| Methyl Trimethicone | 3 |
| Dimethicone | 0.4 |
| Dimethiconol | 0.06 |
| Cyclohexasiloxane | 0.002 |
| Cyclopentasiloxane | 0.002 |
| Ultramarine | 3 |

TABLE 3*-continued

| Ingredient | % Concentration (by weight) |
| --- | --- |
| Silica | 1 |
| Excipients** | q.s. |

*Prepare by mixing the ingredients under heat until uniform and then cool to room temperature (20-25° C.).
**The formulation can be filled out with additional ingredients to have a desired consistency, viscosity, and tactile property. Excipients used for this formula included the following in the following approximate amounts: 3 to 7% by weight of acrylates/ethylhexyl acrylate copolymer; 3 to 7% by weight of alcohol; 3 to 7% by weight of chromium oxide and or iron oxide; 3 to 5% by weight of glyceryl stearate; 2 to 5% by weight of stearic acid; 1 to 3% by weight of methyl methacrylate crosspolymer; 1 to 3% by weight of butylene glycol; 1 to 3% by weight of VP/Eicosene copolymer; 1 to 3% by weight of triethanolamine; 1 to 3% by weight of silica; 0.1 to 1% by weight of propylene glycol; 0.1 to 1% by weight of mica; 0.1 to 1% by weight of diazolidinyl urea; 0.1 to 1% by weight of titanium dioxide; 0.1 to 1% by weight of panthenol; 0.1 to 1% by weight of a dye or colorant; 0.1 to 1% by weight of methyl paraben; 0.001 to 0.2% by weight of tocopheryl acetate; 0.001 to 0.2% by weight of isostearic acid; 0.001 to 0.2% by weight of sodium polymethacrylate; 0.001 to 0.2% by weight of ethylene/methacrylate copolymer; 0.001 to 0.2% by weight of disodium EDTA; 0.001 to 0.2% by weight of phytantriol or hydrolyzed wheat protein; 0.001 to 0.2% by weight of hydrogenated polyisobutene; 0.001 to 0.2% by weight of laureth-21; 0.001 to 0.2% by weight of propylparaben; 0.001 to 0.2% by weight of isopropyl titanium triisostearate; 0.001 to 0.2% by weight of phenoxyethanol; 0.001 to 0.2% by weight of palmitic acid; and 0.001 to 0.2% by weight of benzoic acid.

The Tables 4 and 5 compositions describe water-proof/water-resistant mascaras that were each shown to increase the length of the eyelashes and also increase the volume of a hair shaft while still being easy to apply and remove from the shaft.

TABLE 4*

| Ingredient | % Concentration (by weight) |
| --- | --- |
| Water | 5 |
| Tixogel IDD-1538** | 43 |
| DC 680 ID Fluid*** | 9 |
| Glyceryl Hydrogenated Rosinate | 3 |
| DSPCS/-12**** | 1 |
| Excipients***** | q.s. |

*Prepare by mixing the ingredients under heat until uniform and then cool to room temperature (20-25° C.).
**Commercially available from Southern Clay Products, Inc. (Texas, USA). It is in gel form and has isododecane and quaternium-90 Bentonite.
***Commercially available from Dow Corning Corp. (Michigan, USA). It is a silicone fluid having polypropylsilsesquioxane and isododecane.
****Commercially available from Kobo Products (New Jersey, USA). It is a powder having silica, ethylene/methacrylate copolymer, and isopropyl titanium triisostearate.
*****The formulation can be filled out with additional ingredients to have a desired consistency, viscosity, and tactile property. Excipients used for this formula included the following in the following approximate amounts: 3 to 7% by weight of iron oxide; 3 to 7% by weight of beeswax; 3 to 7% by weight of carnauba wax; 3 to 7% by weight of polyethylene; 1 to 3% by weight of methyl methacrylate crosspolymer; 0.5 to 2% by weight of propylene carbonate; 0.5 to 2% by weight of VP/eicosene copolymer; 0.5 to 2% by weight of phenoxyethanol; 0.5 to 2% by weight of cellulose; 0.5 to 2% by weight of hydrogenated polycyclopentadiene; 0.5 to 2% by weight of capryl glycol; 0.01 to 0.2% by weight of nylon-6; 0.01 to 0.2% by weight of tocopherol acetate; 0.01 to 0.2% by weight of panthenol; 0.01 to 0.2% by weight of butylated hydroxyanisole; and 0.01 to 0.2% by weight of phytantriol.

TABLE 5*

| Ingredient | % Concentration (by weight) |
| --- | --- |
| Water | 5 |
| Tixogel IDD-1538** | 40 |
| DC 680 ID Fluid*** | 9 |
| Glyceryl Hydrogenated Rosinate | 3 |

TABLE 5*-continued

| Ingredient | % Concentration (by weight) |
| --- | --- |
| DSPCS/-12**** | 1 |
| Excipients***** | q.s. |

*Prepare by mixing the ingredients under heat until uniform and then cool to room temperature (20-25° C.).
**Commercially available from Southern Clay Products, Inc. (Texas, USA). It is in gel form and has isododecane and quaternium-90 Bentonite.
***Commercially available from Dow Corning Corp. (Michigan, USA). It is a silicone fluid having polypropylsilsesquioxane and isododecane.
****Commercially available from Kobo Products (New Jersey, USA). It is a powder having silica, ethylene/methacrylate copolymer, and isopropyl titanium triisostearate.
*****The formulation can be filled out with additional ingredients to have a desired consistency, viscosity, and tactile property. Excipients used for this formula included the following in the following approximate amounts: 3 to 7% by weight of iron oxide; 3 to 7% by weight of beeswax; 3 to 7% by weight of carnauba wax; 3 to 7% by weight of polyethylene; 1 to 3% by weight of methyl methacrylate crosspolymer; 1 to 3% by weight of nylon-6; 0.5 to 2% by weight of VP/eicosene copolymer; 0.5 to 2% by weight of propylene carbonate; 0.5 to 2% by weight of silica; 0.5 to 2% by weight of phenoxyethanol; 0.5 to 2% by weight of hydrogenated polycycloepntadiene; 0.5 to 2% by weight of caprylyl glycol; 0.01 to 0.5% by weight of tocopherol acetate; 0.01 to 0.5% by weight of panthenol; 0.01 to 0.5% by weight of phytantriol; and 0.0001 to 0.1% by weight of titanium dioxide.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A mascara primer composition comprising an aqueous base and 1 to 3% by weight of a polymer film former, wherein the aqueous base comprises 85 to 95% by weight of water, and wherein the polymer film former is polyquaternium-69, wherein the composition is formulated as a mascara primer capable of drying within 60 seconds after application to eye lashes, and wherein the composition does not include silica.

2. The mascara primer composition of claim 1, further comprising:
   alcohol;
   triethanolamine;
   acrylic acid/VP crosspolymer;
   PEG-12 dimethicone;
   glycerin;
   benzyl alcohol;
   panthenol;
   chlorphenesin;
   hydroxypropyl cyclodextrin;
   disodium EDTA;
   phytantriol or hydrolyzed wheat protein; and
   iodopropynyl butylcarbamate.

3. The mascara primer composition of claim 2, comprising:
   2 to 4% by weight of alcohol;
   0.5 to 2% by weight of triethanolamine;
   0.5 to 2% by weight of acrylic acid/VP crosspolymer;
   0.5 to 2% by weight of PEG-12 dimethicone;
   0.5 to 2% by weight of glycerin;
   0.1 to 1% by weight of benzyl alcohol;
   0.1 to 1% by weight of panthenol;
   0.1 to 1% by weight of chlorphenesin;
   0.01 to 0.1% by weight of hydroxypropyl cyclodextrin;
   0.01 to 0.1% by weight of disodium EDTA;
   0.01 to 0.1% by weight of phytantriol or hydrolyzed wheat protein; and
   0.001 to 0.1% by weight of iodopropynyl butylcarbamate.

4. The mascara primer composition of claim 1, wherein the composition is transparent and colorless.

5. The mascara primer composition of claim 1, wherein the composition is clear.

6. A mascara composition that is capable of increasing the length of a person's eye lashes, the composition comprising:
   (a) a combination of synthetic fibers, polymeric film formers, and a natural film former in an amount effective to increase the length of the eye lashes; and
   (b) a base,
   wherein the synthetic fibers include nylon 6, the polymeric film formers include PPG-17/IPDI/DMPA Copolymer and Acrylates/Ethylhexyl Acrylate Copolymer, and the natural film former is acacia senegal gum extract, and wherein the composition is formulated as a mascara composition that is capable of increasing the length of a person's eye lashes.

7. The mascara composition of claim 6, wherein the ratio of synthetic fibers to polymeric film formers ranges from 0.10 to 0.30 or from 0.15 to 0.20.

8. The mascara composition of claim 7, wherein the ratio of synthetic fibers to the natural film former ranges from 0.20 to 0.30 or from 0.22 to 0.26.

9. The mascara composition of claim 8, wherein the ratio of polymeric film formers to the natural film former ranges from 1.0 to 2.0 or from 1.0 to 1.5.

10. The mascara composition of claim 6, wherein the composition is formulated as an oil-in-water emulsion, wherein the dispersed oil-phase comprises said polymeric film formers, said natural film former, and further comprises a wax and an emulsifier.

11. The mascara composition of claim 10, further comprising a second dispersed phase that is different from the dispersed oil phase, wherein the second dispersed phase comprises volatile solvents.

* * * * *